(12) United States Patent
Kämmerer et al.

(10) Patent No.: US 8,077,825 B2
(45) Date of Patent: Dec. 13, 2011

(54) JITTER-FREE SPATIAL TRIGGERING OF A DETECTOR OF A CT SYSTEM

(75) Inventors: Peter Kämmerer, Schnaittach (DE); Thomas Reichel, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/770,808

(22) Filed: Apr. 30, 2010

(65) Prior Publication Data

US 2010/0278295 A1 Nov. 4, 2010

(30) Foreign Application Priority Data

May 4, 2009 (DE) .......................... 10 2009 019 841

(51) Int. Cl.
*A61B 6/00* (2006.01)
(52) U.S. Cl. .................................. 378/4; 378/8; 378/19
(58) Field of Classification Search .................. 378/4, 8
See application file for complete search history.

(56) References Cited

U.S. PATENT DOCUMENTS

| | | | | |
|---|---|---|---|---|
| 5,832,051 A | * | 11/1998 | Lutz | 378/8 |
| 6,370,217 B1 | * | 4/2002 | Hu et al. | 378/8 |
| 6,639,965 B1 | * | 10/2003 | Hsieh et al. | 378/8 |
| 2005/0169424 A1 | * | 8/2005 | Bruder et al. | 378/95 |
| 2009/0116612 A1 | * | 5/2009 | Ziegler | 378/9 |

* cited by examiner

*Primary Examiner* — Edward Glick
*Assistant Examiner* — Alexander H Taningco
(74) *Attorney, Agent, or Firm* — Harness, Dickey & Pierce, P.L.C.

(57) ABSTRACT

A method is disclosed for acquiring measured data by way of a computed tomography system, wherein the measured data is acquired by a detector unit disposed opposite the radiation source during a rotation of a radiation source around an examination object. In at least one embodiment, the rotation is subdivided into succeeding time segments during each of which measured data is acquired, and each of the succeeding time segments has either a first length or a second length consisting of two predefined lengths.

16 Claims, 5 Drawing Sheets

JITTER-FREE SPATIAL TRIGGERING OF A DETECTOR OF A CT SYSTEM

PRIORITY STATEMENT

The present application hereby claims priority under 35 U.S.C. §119 on German patent application number DE 10 2007 019 841.5 filed May 4, 2009, the entire contents of which are hereby incorporated herein by reference.

FIELD

At least one embodiment of the invention generally relates to a method for acquiring measured data by way of a computed tomography system.

BACKGROUND

Methods for scanning an examination object by way of a CT system are generally known. In this case circular scans, sequential circular scans with feed, or spiral scans are used for example. With the scans, absorption data or, as the case may be, projections of the examination object are recorded from different recording angles with the aid of at least one X-ray source and at least one oppositely disposed detector, and said thus collected measured data is computed by way of appropriate reconstruction methods into sectional images (slices) through the examination object.

The detectors which serve to capture the measured data are an important component of the CT systems. The rotation of the radiation source around the examination object is subdivided into a multiplicity of succeeding measurement intervals. In order to provide the synchronization of the X-ray detectors that is required for X-ray CT systems, a synchronization input is usually provided on the X-ray detector, the arrival of a sync signal marking the end of the previous and the start of the next measurement interval. The average intensity of the sensor signal between two succeeding sync signals provides a measure for the signal that is subsequently read out. It is important for the image reconstruction that the measured data can be assigned to the respective angular position of its acquisition, i.e. the angular position must be known or be deducible for each measurement interval.

SUMMARY

In at least one embodiment of the invention, a method is disclosed for acquiring measured data by way of a computed tomography system. At least one embodiment is directed to a corresponding control and computing unit, a CT system, a computer program and/or a computer program product.

With the inventive method of at least one embodiment for acquiring measured data by way of a computed tomography system, the measured data is captured by a detector unit disposed opposite a radiation source during a rotation of the radiation source around an examination object. The rotation is subdivided into succeeding time segments during each of which measured data is acquired. Each of the succeeding time segments has either a first length or a second length consisting of two predefined lengths.

The projections are recorded during the rotation of the radiation source. The rotation can be a full rotation, i.e. a rotation through 360°, a partial rotation, i.e. a rotation through less than 360°, such as e.g. a rotation through 180°, or also a plurality of rotations, e.g. as part of a spiral CT recording.

During the rotation measured data is acquired continually, with each acquisition taking place in a time segment, in other words a measurement interval. Said time segments succeed one another directly, preferably without interruption. Owing to the rotation the radiation source moves in the measurement intervals.

Each measurement interval has a specific length. This length is not the same for all measurement intervals. Nor are the lengths of the different measurement intervals distributed in accordance with a distribution scheme, in which case a plurality of different lengths would exist. Rather, there exist two predefined lengths which the measurement intervals can assume. Some of the measurement intervals have the first of the two lengths, while the other measurement intervals have the second of the two lengths.

The lengths to be used for the measurement intervals are specified in advance to the detector unit, preferably by a control and computing unit which preferably can also perform the steps described in the following as embodiments and developments of at least one embodiment of the invention.

In a development of at least one embodiment of the invention it is decided in the course of the rotation which of the two predefined lengths a time segment is to have. In this case, therefore, the length of a measurement interval is not fixed from the start of the rotation on, but rather the length to be set is determined at a later time. This has the advantage that characteristic aspects of the rotational movement which are possibly not predictable can be factored into the decision about the length of the time segments. A decision of said kind concerning the length in the course of the rotation can be made in respect of individual, some or all time segments. A number of options exist for the time of the decision: preferably the decision will be taken directly prior to the start of a time segment, i.e. during the immediately preceding time segment. Alternatively hereto it is, however, also possible to take the decision at an even earlier time than in the immediately preceding time segment.

According to a particularly preferred development of at least one embodiment of the invention, a second subdivision of the rotation into succeeding angle segments having the same angle progression is taken into account in order to decide which of the two predefined lengths a time segment is to have. A subdivision of said kind can be achieved e.g. by generating a pulse signal which indicates the start and end of an angle segment during a rotation at intervals that are equidistant in respect of the angles. The effect of taking the second subdivision into account is that spatial triggering can be adopted as a basis for the time segment lengths that are to be set.

In an embodiment of the invention the time periods required for the rotation vary for the angle segments in the course of the rotation. This means that—although the angle segments are the same size in terms of the angle that the radiation source covers during its rotation—it takes different lengths of time for different angle segments until this constant angle is covered during the rotation. This implies that the rotation is not a movement having a constant angular velocity. Such an effect can be induced e.g. by unbalanced masses.

According to a development of at least one embodiment of the invention, in order to decide which of the two predefined lengths a time segment is to have, a first total is formed from time periods of angle segments covered by the radiation source. In this case the angle segments over which the total is formed can be e.g. those which were covered from the start of the rotation up to the time of the decision, or those which were covered from the start of the rotation up to the time segment whose length is to be decided.

It is particularly advantageous if a second total is formed from lengths of elapsed time segments in order to decide which of the two predefined lengths a time segment is to have. In this case the time segments over which the total is formed can be e.g. those which have elapsed from the start of the rotation up to the time of the decision, or those which have elapsed from the start of the rotation up to the time segment whose length is to be decided.

According to a development of at least one embodiment of the invention, the first and second total are compared with each other. On the basis of the comparison it can be decided which of the two predefined lengths a time segment is to have. It is advantageous if the longer of the two predefined lengths is used for the respective time segment if the second total is less than the first total. In addition or alternatively, the shorter of the two predefined lengths can be used for the respective time segment if the second total is greater than the first total. By comparing the two totals it is possible that on the basis of a suitable choice of the length of the time segments said time segments can lie in such a way that the angle information of a spatial triggering can be used for them.

Furthermore it is possible that each of the succeeding time segments has either a first length or a second length or a third length consisting of three predefined lengths. The method presented is not restricted to the use of precisely two predefined lengths. Rather, a different number, in particular three, can be used.

The detector unit according to at least one embodiment of the invention serves for use in a computed tomography system. The detector unit includes a device for determining lengths for the succeeding time segments such that each time segment has in each case either a first length or a second length consisting of two predefined lengths. In this case, the "device" in the detector unit can be implemented by hardware, e.g. by an FPGA (Field Programmable Gate Array), or by software.

The CT system according to at least one embodiment of the invention includes such a detector unit. It can also contain other components that are required e.g. for acquiring measured data and/or for analyzing measured data.

The computer program according to at least one embodiment of the invention has program code segments that are suitable for controlling the method of the above-described type when the computer program is executed on a computer.

The computer program product according to at least one embodiment of the invention includes program code segments that are stored on a computer-readable data medium and are suitable for controlling the method of the above-described type when the computer program is executed on a computer.

BRIEF DESCRIPTION OF THE DRAWINGS

The invention is explained in more detail below with reference to an example embodiment and the attached figures, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
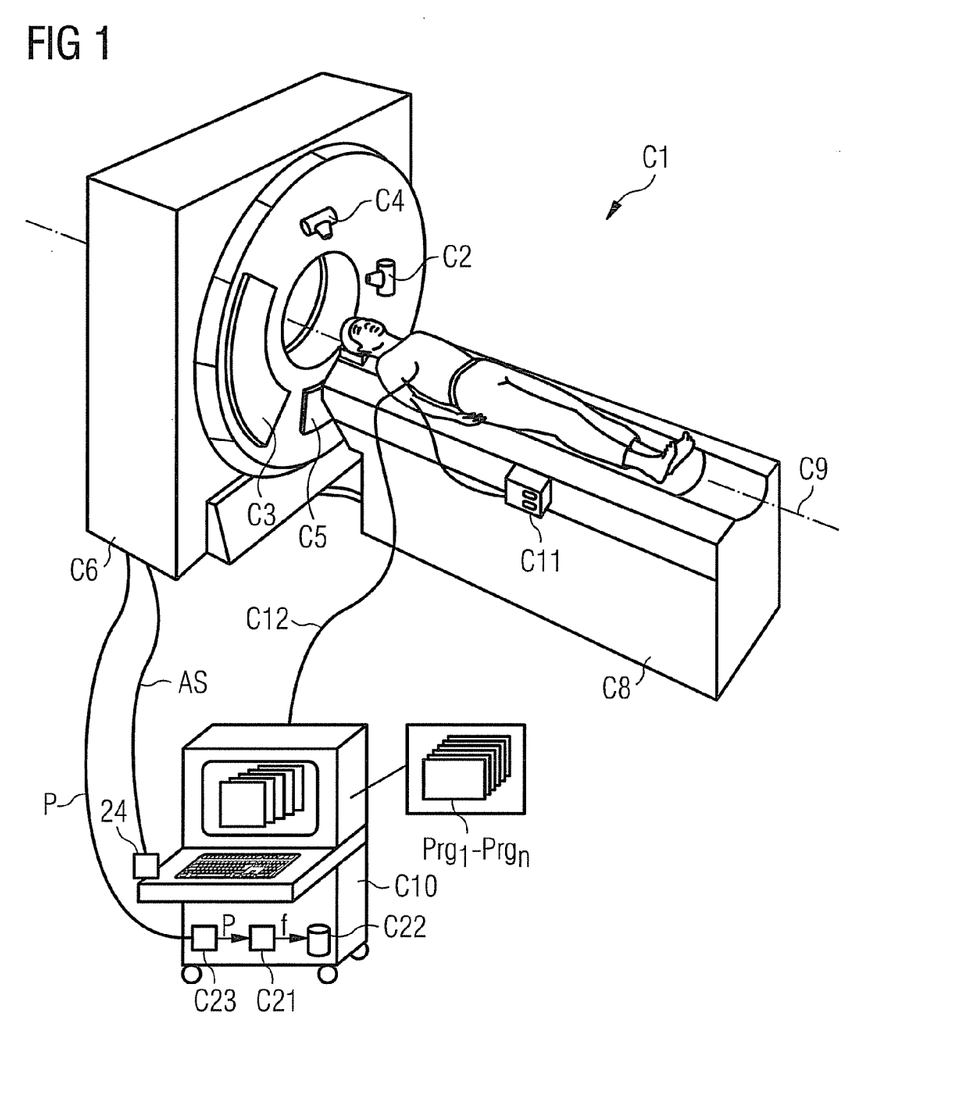
FIG. 1: shows a first schematic view of an example embodiment of a computed tomography system.

FIG. 1 first shows a schematic view of a first computed tomography system C1 having an image reconstruction apparatus C21. Contained in the gantry housing C6 is a closed gantry (not shown here) on which a first X-ray tube C2 having an oppositely disposed detector C3 is arranged. Optionally, a second X-ray tube C4 having an oppositely disposed detector C5 is arranged in the CT system shown here, thereby enabling a higher time resolution to be achieved based on the additionally available radiation source/detector combination, or, if different X-ray energy spectra are used in the radiation source/detector systems, also enabling "dual energy" examinations to be performed.

The CT system C1 additionally has a patient table C8 on which a patient can be moved during the examination along a system axis C9, also referred to as the z-axis, into the measurement field, wherein the scan itself can take place both as a pure circular scan without patient feed exclusively in the examination region of interest. In this case the X-ray source C2 or, as the case may be, C4 in each case rotates around the patient. In parallel therewith the detector C3 or, as the case may be, C5 co-rotates with the X-ray source C2 or, as the case may be, C4 in order to acquire projection measured data which is then used to reconstruct slices. As an alternative to a sequential scan, in which the patient is moved incrementally through the examination field between the individual scans, it is of course also possible to perform a spiral scan, in which the patient is moved during the circular scanning by way of the X-ray radiation continuously along the system axis C9 through the examination field between X-ray tube C2 or, as the case may be, C4 and detector C3 or, as the case may be, C5. With a spiral scan, the movement of the patient along the axis C9 and the simultaneous rotation of the X-ray source C2 or, as the case may be, C4 cause the X-ray source C2 or, as the case may be, C4 to follow a helical path relative to the patient during the measurement.

The CT system 10 is controlled by way of a control and computing unit C10 having computer program code $Prg_1$ to $Prg_n$ residing in a memory. Acquisition control signals AS can be transmitted from the control and computing unit C10 via a control interface 24 in order to control the acquisition of the measured data p by way of the CT system C1.

The projection measured data p acquired by the detector C3 or, as the case may be, C5 is passed to the control and computing unit C10 via a raw data interface C23. Following suitable preprocessing where appropriate, the measured data is then processed further in an image reconstruction component C21. In the present example embodiment the image reconstruction component C21 is implemented in the control and computing unit C10 in the form of software on a processor, e.g. in the form of one or more of the computer program codes $Prg_1$ to $Prg_n$. The image data f reconstructed by the image reconstruction component C21 is then stored in a memory C22 of the control and computing unit C10 and/or output in the conventional manner on the monitor of the control and computing unit C10. It can also be fed via an interface (not shown in FIG. 1) into a network connected to the computed tomography system C1, a radiological information system (RIS) for example, and stored in a mass storage device that is accessible there or output as images.

In addition the control and computing unit C10 can also perform the function of an ECG, a cable C12 being used between patient and control and computing unit C10 to derive the ECG potentials. In addition the CT system C1 shown in FIG. 1 also has a contrast agent injector C11 via which contrast agent can additionally be injected into the patient's bloodstream so that the vessels of the patient, in particular the ventricles of the beating heart, can be visualized more clearly. Furthermore this also affords the possibility of performing perfusion measurements, to which the proposed method is likewise suited.

Figure 2:
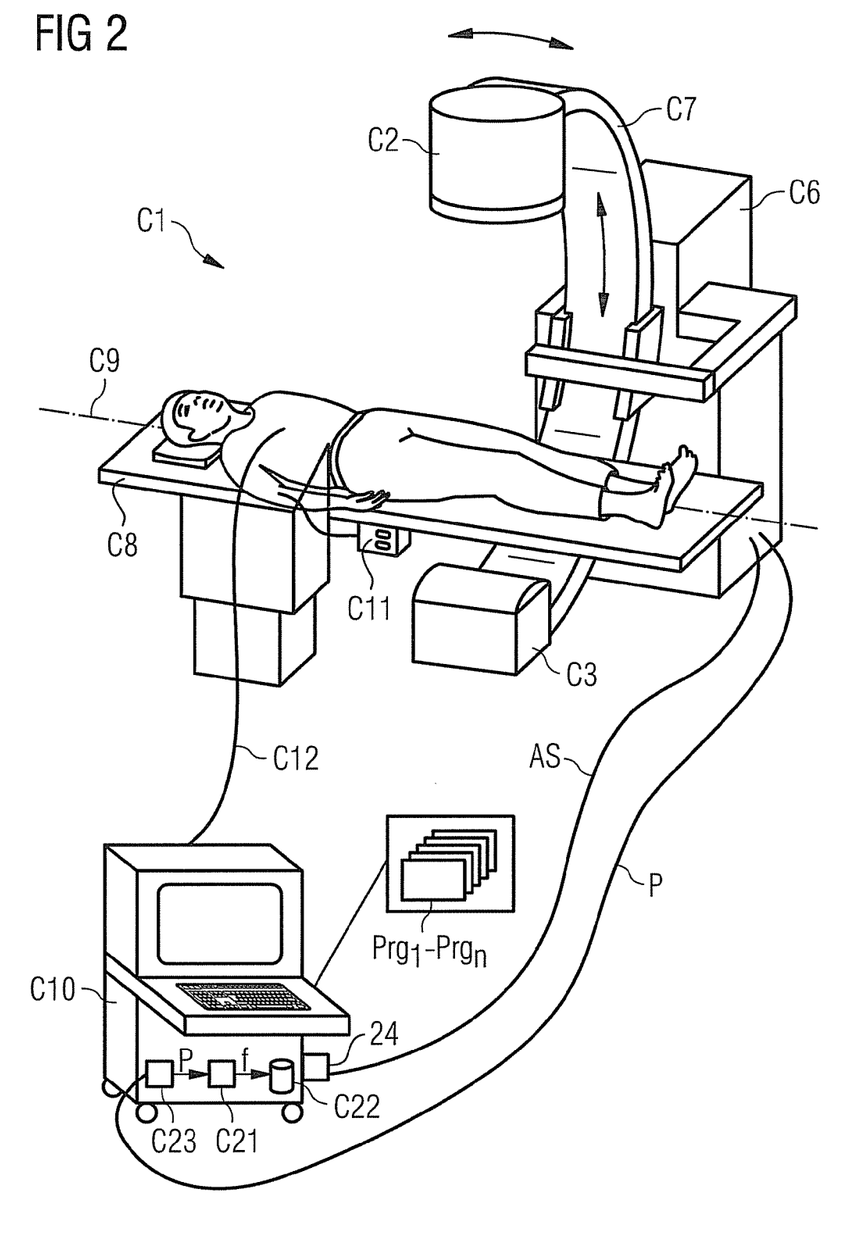
FIG. 2: shows a second schematic view of an example embodiment of a computed tomography system.

FIG. 2 shows a C-arm system in which, in contrast to the CT system shown in FIG. 1, the housing C6 carries the C arm C7 to which the X-ray tube C2 is secured on one side and the oppositely disposed detector C3 is secured on the other side. To perform a scan the C arm C7 is likewise pivoted around a system axis C9 so that scanning can take place from a plurality of scanning angles and corresponding projection data p can be determined from a plurality of projection angles. The C-arm system C1 of FIG. 2, like the CT system from FIG. 1, has a control and computing unit C10 of the type described with reference to FIG. 1.

Embodiments of the invention can be applied in both of the systems shown in FIGS. 1 and 2. Furthermore it can also be used in principle for other CT systems, e.g. for CT systems having a detector forming a complete ring.

Figure 3:
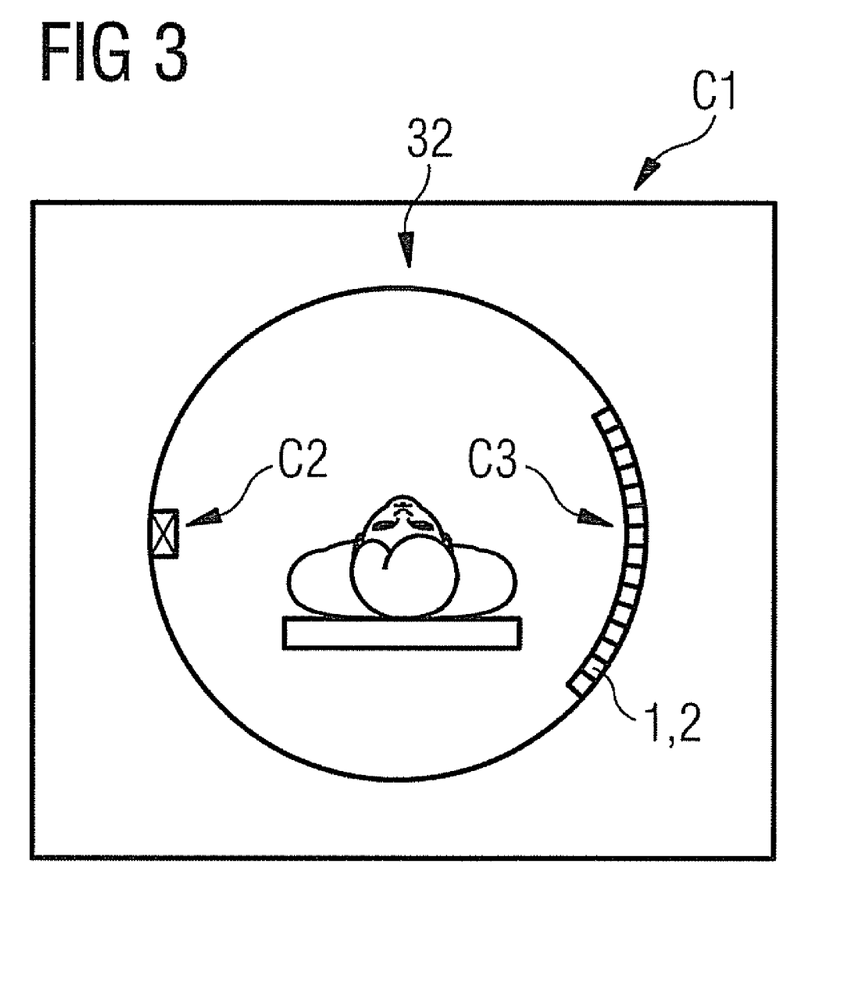
FIG. 3: shows a side view of the first example embodiment of a computed tomography system.

FIG. 3 shows a cross-section of the computed tomography system C1 from FIG. 1. The detector C3 is constructed from a plurality of detector modules 1, 2 which are arranged in series along a detector ring 32. The X-ray tube C2 is arranged diametrically on the opposite side of the detector ring 32. During operation of the computed tomography system C1 the X-ray tube C2 and the detector C3 rotate around the examination object, in particular around a patient to be examined. In the process X-ray images of the examination object are recorded from different directions. Radiation that has passed through the examination object strikes the detector C3. The detector C3 generates signals corresponding to the intensity of the incident radiation.

It must be possible to assign the radiation detected by the detector modules 1, 2 to the angular position of the acquisition of the respective projection. This angle information is required for the image reconstruction method in order to enable an image of the examination object to be calculated. For that purpose the rotation of the detector around the examination object is subdivided into individual, immediately succeeding time segments or, as the case may be, measurement intervals which are referred to hereinafter as integration cycles. During an integration cycle the X-ray quanta are "counted" by the detector modules 1, 2, this measured value being assigned to the mean projection angle at which the gantry was located during the respective integration cycle. A full rotation through 360° can comprise 1500 to 2000 integration cycles for example. Each integration cycle has a length of typically between 200 and 400 µs. By way of the detector triggering it is specified in advance to the detector when an integration cycle starts, and when it ends, i.e. when the next integration cycle starts.

There are two different types of detector triggering, which are presented below:

Time triggering is characterized by scans that are equidistant in time. On the basis of a time measurement it is therefore decided when an integration cycle will start and when it will end. This means that in the case of time triggering all the integration cycles have exactly the same length. This is shown in the histogram representation of FIG. 4A. The integration time, i.e. the length of the integration cycles, is plotted in μs on the abscissa. How frequently the respective duration of the integration cycles has occurred within a complete revolution is plotted on the ordinate. Because of the time triggering only the value 215 μs exists. The lengths of all the integration cycles in the course of the measurement are therefore identical. This is advantageous for the processing electronics connected downstream of the detector. However, it is disadvantageous that initially no relationship exists between the integration cycle and the respective projection angle. Since it is complicated to complete this angular relationship in the course of the image reconstruction, pure time triggering should be avoided.

Figure 4A:
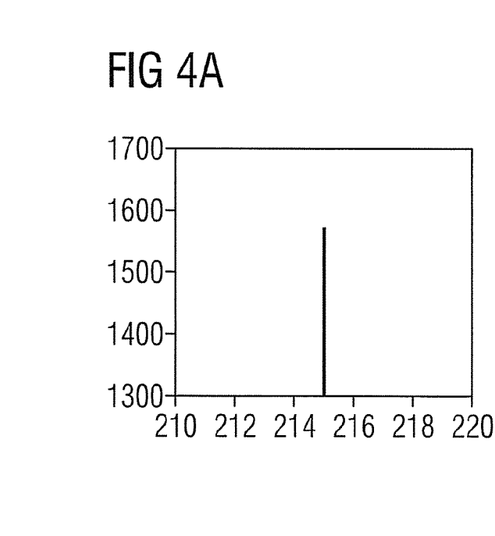
FIG. 4: shows lengths of integration cycles for different types of detector triggering in a histogram representation.
Figure 4B:
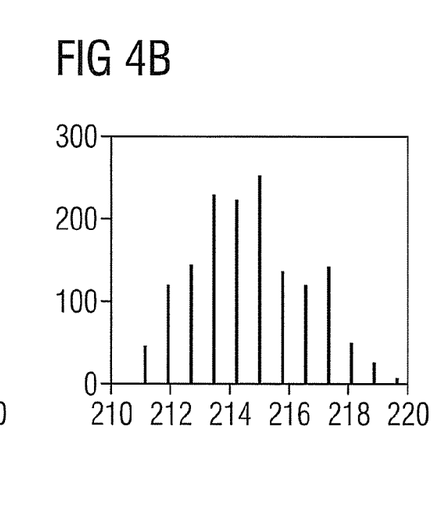

With spatial triggering, on the other hand, when an integration cycle starts and when it ends is decided on the basis of a spatial measurement. During the rotation of the gantry angle pulses are made available at constant angle intervals using angle markers. Each angle pulse triggers the start of an integration cycle. As a result of this there exists a direct angular relationship between the respective measurement and the examination object. However, it is disadvantageous that due to mechanical inadequacies such as existing unbalanced masses, for example, as well as mechanically not exactly uniformly distributed angle markers, no scans that are equidistant in time are produced. This is shown in FIG. 4B. In FIG. 4B, as in FIG. 4A, the integration time is also plotted in μs on the abscissa, and the frequency of the respective length of the integration cycle is plotted on the ordinate. It can be seen that a distribution of the values around a mean value of 215 μs is produced due to the jitter caused by the spatial triggering.

This distribution of the lengths of the integration cycles is of great disadvantage for the analysis electronics. The scheduling control of the overall detector electronics is more complicated due to the individual handling of every single, temporally different measurement interval. Moreover there are commercially available converter devices which explicitly require one measurement interval or a small number of temporally identical measurement intervals. The use of said devices is therefore ruled out in the case of spatial triggering.

These disadvantages can only be corrected with substantial overhead and significantly limit the available AD converter concepts and consequently the ASICs that can be used.

FIGS. 5A and 5B again illustrate the effect of pure spatial triggering. In this case FIG. 5B is an enlarged detail from FIG. 5A. The number of the integration cycle is plotted to the right in each case, and the respective length in μs to the top. The legend of the abscissa for FIGS. 5A, 5C and 5E can be found under FIG. 5E, and for FIGS. 5B, 5D and 5F under FIG. 5F. A partial rotation through approx. 270° with 1500 angle pulses or, as the case may be, integration cycles is considered. It can be seen with reference to FIGS. 5A and 5B that the length of the integration cycles varies in the case of spatial triggering.

Figure 5A:
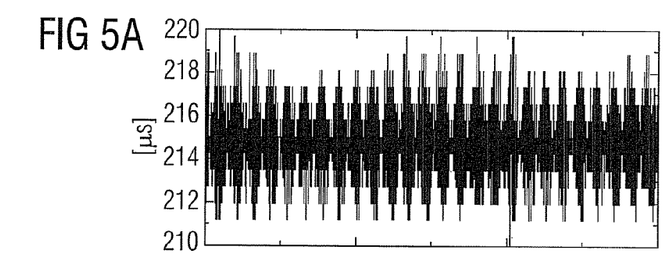
FIG. 5: shows lengths of integration cycles in the course of a rotation of a CT device; on the left in overview, and on the right a detail from the overview.
Figure 5B:
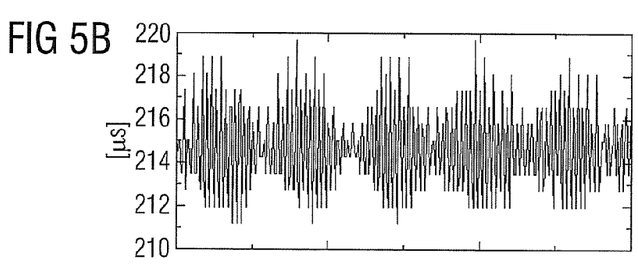
Figure 5C:
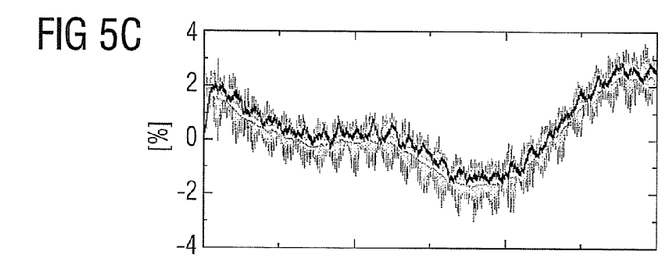
Figure 5D:
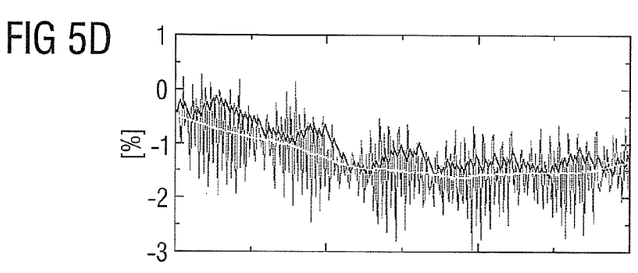

Starting from FIGS. 5A and 5B, the light gray curve of FIGS. 5C and 5D is arrived at by adding together the integration times of FIGS. 5A and 5B respectively and comparing them with the case where all the integration cycles have the length 217 μs.

Referred to a specific integration cycle with the number x, therefore, on the one hand the lengths of all integration cycles with numbers less than or equal to x are added to the spatial triggering according to FIG. 5A or 5B, and on the other hand the length 217 μs is multiplied by the number of integration cycles with numbers less than or equal to x. The difference between these two quantities—referred to the length 217 μs—is plotted on the ordinate of FIGS. 5C and 5D as a light gray curve. The white curve is a moving mean over the gray curve. The moving mean is used because the small-scale variations in the mechanical scanning are effectively masked out thereby.

Figure 4C:
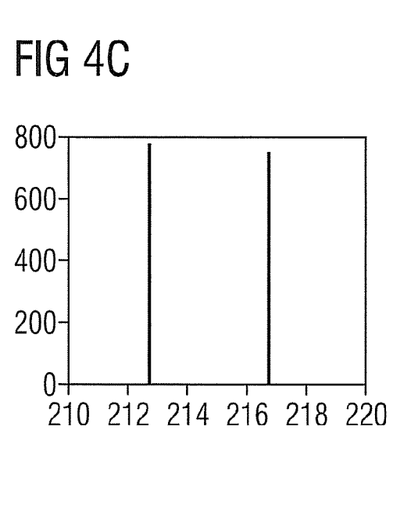

In the following it is described how the disadvantages of spatial triggering illustrated with reference to FIG. 4B can be avoided without the necessity of resorting to the time triggering described with reference to FIG. 4A. As can be seen in the histogram of FIG. 4C, precisely two possible lengths for the integration cycles are predefined for this purpose. The axes of FIG. 4C correspond to those of FIGS. 4A and 4B. These two lengths are chosen so as to be favorable for the analysis electronics. Other time periods for the integration cycles are not permitted.

Figure 5E:
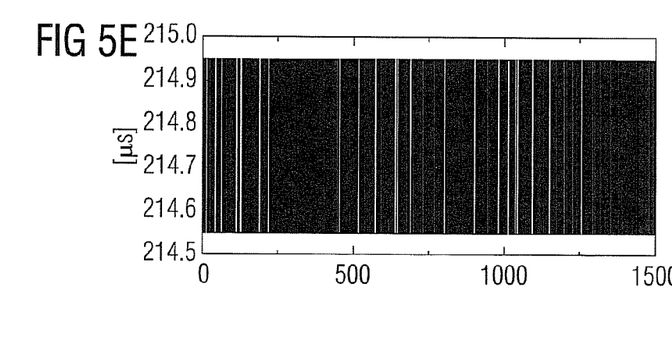
Figure 5F:
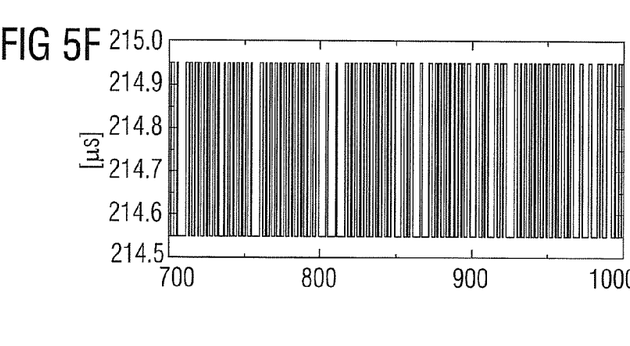

FIGS. 5E and 5F show how only precisely two lengths are ever used for the integration cycles. (The actual numeric examples of FIGS. 4 and 5 differ from one another.) In this case, however, the two predefined lengths are not simply used in alternation. Rather, an attempt is made to decide on the value to be used for the lengths in each case in such a way that the angle information is as accurate as possible or, as the case may be, that the angle error is as small as possible, i.e. each integration cycle is to be assigned the appropriate angular position. This corresponds to the attempt to obtain a curve which matches the white curve of FIGS. 5C and 5D as accurately as possible despite the use of only two lengths. The curve that is produced when the two lengths are used is entered in black in FIGS. 5C and 5D. It can be seen that the black line follows the white line at a very short distance, the difference being less than 1% of a measurement interval. The black curve is therefore adjusted to the white curve, and moreover without the latter being used in the system. This has the further advantage that the great fluctuations that occur in the gray curve can be avoided.

The following approach is adopted in order to decide which of the two lengths is to be used: upon arrival of an angle pulse the time that has elapsed starting with the first angle pulse up to the angle pulse is added; this corresponds to the gray curve in Figures 5c and 5D, although the latter—as described above—is referred to the deviation from the length 217 μs. Furthermore, starting with the first angle pulse up to this angle pulse, the length used in each case out of the two predefined lengths is also added. If this second total is less than the first, the longer of the two times is used for the next integration cycle, whereas if the second total is greater than the first, the shorter of the two times is used for the next integration cycle. What is achieved in this way is that for each integration cycle the angle information corresponding to the angle pulses and consequently to the spatial triggering—which is not used here—can be correctly assigned to the respective integration cycle. Subsequently adding angle information as in the case of pure time triggering is therefore not necessary.

It can be seen with reference to FIGS. 5C and 5E or, as the case may be, with reference to FIGS. 5D and 5F that when two only slightly different integration times are used which differ from each other by only 0.2 μs, i.e. 0.1% of the nominal value of 217 μs, it is possible to follow variations in the range of +/−2% and more.

The described approach therefore combines the advantages of the above-explained time triggering and spatial triggering: On the one hand, as also in the case of time triggering, the analysis electronics is accommodated in that only lengths which can be handled effectively and without error are used for the integration cycles. Compared with spatial triggering, therefore, the fine discretization of the integration cycle lengths is eliminated in favor of a rough discretization. On the other hand the angle information of the spatial triggering is used in order to decide which of the two lengths will be used for the respective integration cycle so that the respective angle information can be assigned directly to the respective measured data.

The invention has been described hereintofore with reference to an exemplary embodiment. It goes without saying that numerous changes and modifications are possible without leaving the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for acquiring measured data by way of a computed tomography system, comprising:
subdividing a rotation, of a radiation source around an examination object by a detector unit disposed opposite the radiation source, into succeeding time segments; and
acquiring the measured data during each of the succeeding time segments, each of the succeeding time segments including either a first length or a second length including two predefined lengths wherein, in order to decide which of the two predefined lengths a time segment is to have, a second subdivision of the rotation into succeeding angle segments having the same angle progression is taken into account.

2. The method as claimed in claim 1, wherein it is decided, in the course of the rotation, which of the two predefined lengths a time segment is to have.

3. The method as claimed in claim 2, wherein the time periods required for the rotation vary for the angle segments in the course of the rotation.

4. The method as claimed in claim 3, wherein, in order to decide which of the two predefined lengths a time segment is to have, a first total is formed from the time periods of angle segments covered by the radiation source.

5. The method as claimed in claim 1, wherein the time periods required for the rotation vary for the angle segments in the course of the rotation.

6. The method as claimed in claim 5, wherein, in order to decide which of the two predefined lengths a time segment is to have, a first total is formed from the time periods of angle segments covered by the radiation source.

7. The method as claimed in claim 6, wherein in order to decide which of the two predefined lengths a time segment is to have, a second total is formed from lengths of elapsed time segments.

8. The method as claimed in claim 7, wherein the first total and the second total are compared with each other.

9. The method as claimed in claim 8, wherein a relatively longer of the two predefined lengths is used for the respective time segment if the second total is less than the first total.

10. The method as claimed in claim 9, wherein a relatively shorter of the two predefined lengths is used for the respective time segment if the second total is greater than the first total.

11. The method as claimed in claim 8, wherein a relatively shorter of the two predefined lengths is used for the respective time segment if the second total is greater than the first total.

12. The method as claimed in claim 1, wherein each of the succeeding time segments has either a first length or a second length or a third length consisting of three predefined lengths.

13. The method as claimed in claim 1, wherein, in order to decide which of the two predefined lengths a time segment is to have, a first total is formed from the time periods of angle segments covered by the radiation source.

14. A detector unit for a computed tomography system, the detector unit being disposed opposite a radiation source in the computer tomography system and being adapted to acquire measured data during a rotating movement of the radiation source around an examination object, the rotation being subdivided into a series of succeeding time segments during each of which the measured data is acquired, the detector unit comprising at least one device to determine lengths for the succeeding time segments such that each time segment includes, in each case, either a first length or a second length consisting of two predefined lengths wherein, in order to decide which of the two predefined lengths a time segment is to have, a second subdivision of the rotation into succeeding angle segments having the same angle progression is taken into account.

15. A CT system comprising the detector unit as claimed in claim 14.

16. A computer program product, comprising program code segments of a computer program that are stored on a non-transitory computer-readable data medium, for controlling the method as claimed in claim 1 when the computer program is executed on a computer.

* * * * *